United States Patent
Dafinger et al.

(10) Patent No.: US 8,710,259 B2
(45) Date of Patent: Apr. 29, 2014

(54) METHOD FOR PRODUCING VINYL ACETATE MONOMER

(75) Inventors: Willibald Dafinger, Röhrnbach (DE); Peter Holl, Emmerting (DE); Johann Wagner, Burghausen (DE)

(73) Assignee: Wacker Chemie AG, Munich (DE)

( * ) Notice: Subject to any disclaimer, the term of this patent is extended or adjusted under 35 U.S.C. 154(b) by 351 days.

(21) Appl. No.: 13/266,324

(22) PCT Filed: Apr. 22, 2010

(86) PCT No.: PCT/EP2010/055348
§ 371 (c)(1),
(2), (4) Date: Oct. 26, 2011

(87) PCT Pub. No.: WO2010/124985
PCT Pub. Date: Nov. 4, 2010

(65) Prior Publication Data
US 2012/0053361 A1     Mar. 1, 2012

(30) Foreign Application Priority Data

Apr. 27, 2009 (DE) .......................... 10 2009 002 666

(51) Int. Cl.
*C07C 67/05* (2006.01)
(52) U.S. Cl.
CPC ..................................... *C07C 67/05* (2013.01)
USPC ........................................ 560/248; 560/261
(58) Field of Classification Search
None
See application file for complete search history.

(56) References Cited

U.S. PATENT DOCUMENTS

2008/0004467 A1    1/2008  Dafinger

FOREIGN PATENT DOCUMENTS

| DE | 102006038689 A1 | 2/2008 |
|----|-----------------|--------|
| EP | 1642882 A2 | 4/2006 |
| WO | 2005100296 A1 | 10/2005 |
| WO | 2008019873 A1 | 2/2008 |

OTHER PUBLICATIONS

International Search Report issued in PCT/EP2010/055348 filed Apr. 22, 2010, mailed Jun. 30, 2010.

*Primary Examiner* — Michael Barker
(74) *Attorney, Agent, or Firm* — RatnerPrestia

(57) ABSTRACT

The invention relates to a method for producing vinyl acetate in a heterogeneously catalyzed, continuous gas-phase process by reacting ethylene with acetic acid and oxygen in a reactor, and a) separating the product gas flow essentially containing ethylene, vinyl acetate, acetic acid, water, carbon dioxide, and other inert gases, and b) feeding a circulating gas flow containing ethylene and $CO_2$ back into the reactor, c) the circulating gas flow being compressed in a circulating gas compressor before being fed back into the reactor, and d) a partial flow of the circulating gas is branched off on the suction side or the pressure side of the circulating gas compressor and is fed to a $CO_2$ scrubbing process, and e) is scrubbed in a water scrubber before the $CO_2$ scrubbing process, characterized in that f) after the $CO_2$ scrubbing process, the partial flow, together with ethylene as a propellant, is fed, by means of a jet compressor, to the circulating gas on the pressure side of the circulating gas compressor and downstream of the point where the partial flow is removed for $CO_2$ scrubbing, and/or g) the bottom product from the water scrubber is fed directly to the pre-dehydration column.

8 Claims, 1 Drawing Sheet

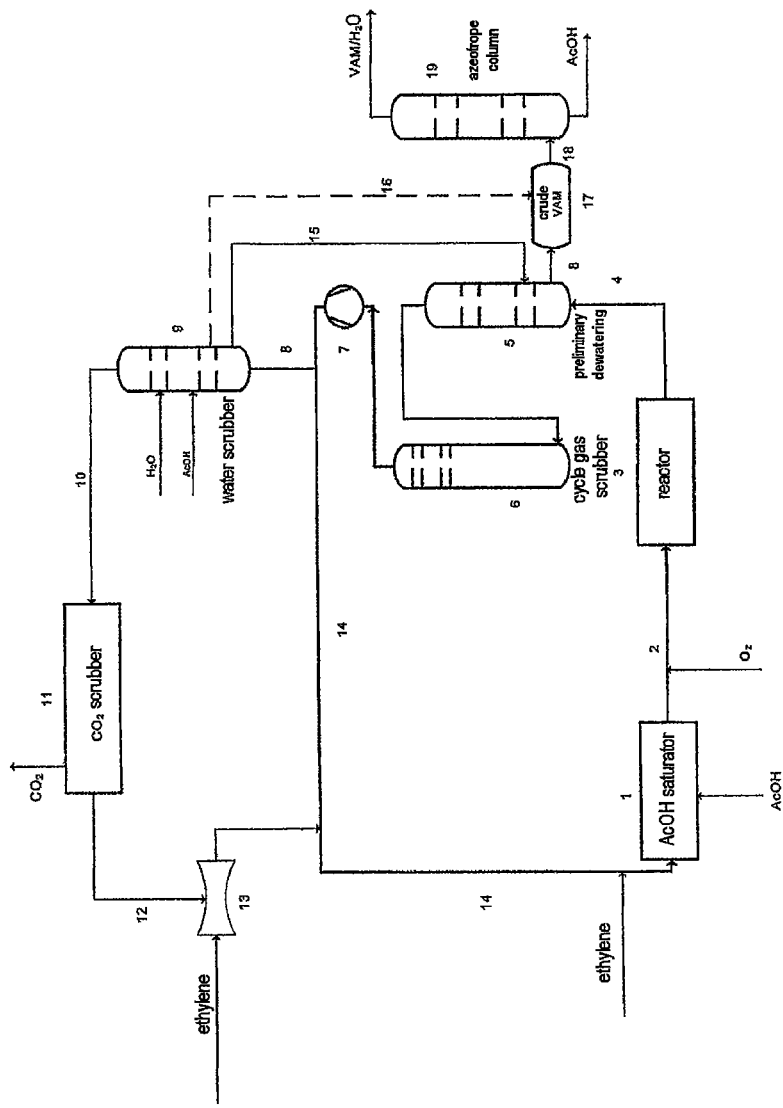

METHOD FOR PRODUCING VINYL ACETATE MONOMER

CROSS REFERENCE TO RELATED APPLICATIONS

This application is the national phase filing of international patent application No. PCT/EP2010/055348, filed 22 Apr. 2010, and claims priority of German patent application number 10 2009 002 666.5, filed 27 Apr. 2009, the entireties of which applications are incorporated herein by reference.

FIELD OF THE INVENTION

The invention relates to a process for preparing vinyl acetate monomer in a heterogeneously catalysed, continuous gas phase process by reacting ethylene with acetic acid and oxygen in a reactor, wherein the workup of the product stream obtained is energetically optimized.

BACKGROUND OF THE INVENTION

Vinyl acetate monomer is prepared in continuous processes with recycling of the purified product stream (cycle gas system). In a heterogeneously catalysed gas phase process, ethylene reacts with acetic acid and oxygen over fixed bed catalysts which generally comprise palladium salts and alkali metal salts on a support material and may additionally also be doped with gold, rhodium or cadmium.

The ethylene, oxygen and acetic acid reactants are converted in an exothermic reaction, generally at a pressure of 1 to 30 bar and a temperature of 130° C. to 200° C., in a fixed bed tubular reactor (or else fluidized bed reactor) to vinyl acetate monomer:

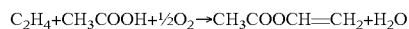

In the side reaction, ethylene is oxidized to $CO_2$:

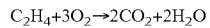

In the preparation of vinyl acetate monomer, a gas mixture consisting predominantly of ethylene, carbon dioxide, ethane, nitrogen and oxygen is circulated. Upstream of the fixed bed tubular reactor, the gas stream is admixed with the acetic acid, ethylene and oxygen reactants and brought to reaction temperature with steam-operated heat exchangers. The cycle gas is enriched with acetic acid upstream of the fixed bed tubular reactor, typically by means of a steam-operated acetic acid saturator (acetic acid evaporator).

The product gas stream leaving the reactor comprises essentially vinyl acetate monomer, ethylene, acetic acid, water, oxygen, $CO_2$, and the inerts: nitrogen, argon, methane and ethane. After the reaction, the vinyl acetate monomer reaction product, unconverted acetic acid, water and further condensable components are condensed out of the cycle gas and sent to workup. Uncondensed vinyl acetate monomer is scrubbed out in an acetic acid-operated scrubber. The condensed vinyl acetate monomer and water products and unconverted acetic acid are separated from one another in different, typically steam-operated distillation processes and the remaining ethylene-containing cycle gas is returned after compression.

A substream of the cycle gas is, before being recycled into the reactor, branched off on the pressure side of the cycle gas compressor, supplied to the $CO_2$ removal of the $CO_2$ scrubber ($CO_2$ absorption/desorption) and, after the $CO_2$ removal, returned back to the suction side of the compressor. Before the $CO_2$ removal, this substream is typically freed of vinyl acetate monomer in a column (water scrubber) by means of addition of acetic acid and water. The bottom product of this column, which comprises water, acetic acid and VAM, is separated in the azeotrope column which is heated with process steam.

A problem in the process steps for $CO_2$ scrubbing is the necessity to return the substream on the suction side owing to the pressure drops which occur in the course of scrubbing, with the disadvantage that the entire substream has to be compressed once again (additional compressor load). The suction-side recycling additionally requires that, after the compression, the already purified substream is supplied again to the unpurified cycle gas stream and partly fed back to the $CO_2$ scrubbing.

A further disadvantage of the process steps for $CO_2$ scrubbing practised to date is the energy expenditure to separate the crude vinyl acetate monomer obtained after the scrubbing in the cycle gas scrubber in an azeotrope column.

Against this background, it was an object of the present invention to energetically optimise the workup of the substream branched off for $CO_2$ scrubbing.

DE 10 2006 038 689 A1 discloses using the heat content of the steam-saturated $CO_2$ stream obtained from the carbon dioxide desorber in the $CO_2$ scrubbing to heat the bottom of the pure vinyl acetate monomer column. A disadvantage is the poor heat transfer when a gaseous heat transfer medium is used. Moreover, the heat content of this $CO_2$ steam is very low owing to the relatively low proportion of steam.

SUMMARY OF THE INVENTION

The invention provides a process for preparing vinyl acetate monomer in a heterogeneously catalysed, continuous gas phase process by reacting ethylene with acetic acid and oxygen in a reactor, and
a) separating the product gas stream comprising essentially ethylene, vinyl acetate monomer, acetic acid, water, carbon dioxide and further inert gases, and
b) recycling an ethylene- and $CO_2$-containing cycle gas stream into the reactor, by
c) compressing the cycle gas stream in a cycle gas compressor before recycling into the reactor, and
d) branching off a substream of the cycle gas on the suction side or the pressure side of the cycle gas compressor and feeding it to a $CO_2$ scrubbing, and
e) prior to the $CO_2$ scrubbing, washing it in a water scrubber, characterized in that
f) the substream, after the $CO_2$ scrubbing, is supplied to the cycle gas via a jet compressor, together with ethylene as the motive medium, on the pressure side of the cycle gas compressor and downstream of the withdrawal of the substream to the $CO_2$ scrubbing, and/or
g) the bottom product from the water scrubber is fed directly to the preliminary dewatering column.

BRIEF DESCRIPTION OF THE DRAWING

FIG. 1 shows a simplified diagram of a process for making vinyl acetate monomer according to the invention.

DETAILED DESCRIPTION OF THE INVENTION

The continuous preparation of vinyl acetate monomer is preferably conducted in tubular reactors charged with a fixed bed catalyst. These catalysts are generally supported catalysts doped with noble metals or noble metal salts and promoters, for example bentonite spheres doped with palladium and with gold and potassium salts. The reactor is charged with ethylene, oxygen and acetic acid, and the reaction is performed at a pressure of preferably 8 to 12 bar abs. and a temperature of preferably 130° C. to 200° C.

The reaction temperature in the fixed bed tubular reactor of preferably 130° C. to 200° C. is set by means of evaporative water cooling at a pressure of 1 to 30 bar abs. This forms steam, known as the intrinsic steam, with a temperature of 120° C. to 185° C., at a pressure of 1 to 10 bar abs., preferably 2.5 to 5 bar abs. The product gas stream emerging from the reactor comprises essentially vinyl acetate monomer, ethylene, acetic acid, water, oxygen, $CO_2$, and the inerts: nitrogen, argon, methane and ethane.

In general, the gas mixture leaving the fixed bed tubular reactor is passed into a preliminary dewatering column and the liquid phase obtained at the bottom of the column, principally vinyl acetate monomer, acetic acid, ethyl acetate and water, is fed to the crude vinyl acetate monomer collecting vessel. In the downstream azeotrope column, it is separated into vinyl acetate monomer (VAM) and water as the top product, and acetic acid as the bottom product. The acetic acid is passed into the acetic acid saturator and thus recycled into the process. The VAM withdrawn as the top product is passed via the dewatering column to the pure vinyl acetate monomer column and separated there into VAM and acetic acid.

The gaseous product mixture withdrawn at the top of the preliminary dewatering column, consisting essentially of ethylene and $CO_2$, is freed in the cycle gas scrubber from all condensable components. The cycle gas stream withdrawn at the top of the cycle gas scrubber is compressed in the cycle gas compressor to compensate for the considerable pressure drops which occur in the reaction. circuit, and recycled into the reactor as cycle gas. The pressure level of the cycle gas is preferably 8 to 12 bar abs. After the removal of the condensable vinyl acetate monomer, acetic acid and water components in the cycle gas scrubber, the cycle gas contains preferably 12 to 18% by volume of $CO_2$.

A substream of the cycle gas is branched off on the suction side or pressure side, preferably the pressure side, of the cycle gas compressor and fed to the $CO_2$ removal of the $CO_2$ scrubbing and, after the $CO_2$ removal, is returned back to the pressure side of the compressor. The substream withdrawn in the cycle gas compressor makes up about 8 to 12% by volume of the overall cycle gas. Downstream of the branch and upstream of the $CO_2$ scrubber, the substream withdrawn is scrubbed in a column (water scrubber) with supply of water and acetic acid. The liquid bottom product can be collected in the crude vinyl acetate monomer vessel and separated in the downstream azeotrope column. The gaseous top product of the water scrubber, essentially ethylene and $CO_2$, is fed to the $CO_2$ scrubbing.

The cycle gas substream (top product from the water scrubber) is then conducted into a $CO_2$ absorption/desorption, preferably operated with aqueous potassium carbonate solution. After the $CO_2$ scrubbing, the cycle gas substream preferably still contains 2 to 6% by volume of $CO_2$. The pressure drop after cycle gas scrubbing and $CO_2$ absorption/desorption is generally 2 to 4 bar.

The cycle gas substream is recycled into the cycle gas stream downstream of the $CO_2$ scrubbing, on the pressure side of the cycle gas compressor, and downstream of the withdrawal point of the substream to the $CO_2$ scrubbing. To compensate for the pressure drop, the cycle gas substream is brought by means of ethylene, which is obtained from the refinery with a pressure of 20 to 25 bar abs., to a pressure level of preferably 0.5 to 2 bar above the pressure of the cycle gas, and supplied to the cycle gas stream. The cycle gas stream is preferably supplied with the required amount of ethylene via a jet compressor (ejectors, injectors), preferably a suction nozzle. In a preferred embodiment, it is also possible to proceed in such a way that the entire ethylene feed which is supplied to the cycle gas upstream of the reactor is supplied via the jet compressor.

Alternatively to this procedure of recycling the cycle gas substream, or in addition thereto, it is also possible to proceed in such a way that the operation of the water scrubber upstream of the $CO_2$ absorption/desorption is reconfigured in accordance with the invention. The water scrubber is preferably operated at a pressure of 8 to 12 abs. and a temperature of preferably 18 to 30° C. The cycle gas substream is freed of VAM in the water scrubber by means of acetic acid and freed of entrained acetic acid by means of water. At the top, the gaseous residual proportion of the cycle gas substream is withdrawn and conducted to the $CO_2$ scrubbing.

In the inventive modification, the liquid phase obtained at the bottom of the water scrubber, principally vinyl acetate monomer, acetic acid, ethyl acetate and water, is no longer fed to the crude vinyl acetate monomer collecting vessel and separated in the azeotrope column, but rather applied directly to the preliminary dewatering column. In this case, the bottom product is preferably heated by heat exchange with the gaseous product stream emerging from the reactor. In the preliminary dewatering column, a VAM-water azeotrope is then obtained without using external steam and subsequently separated in a phase separator. The steam saving achievable by this measure for the removal of the water supplied to the water scrubber is at a weight ratio of steam/water of about 2:1. By means of this measure, in an industrial scale plant, at a water flow rate of 300 to 500 kg of water/hour, a steam saving of about 1 to/h in the azeotrope column is achieved.

FIG. 1 shows a simplified diagram of the process: ethylene-containing cycle gas was contacted with acetic acid in the acetic acid saturator 1, then oxygen was added and the mixture was fed to the tubular reactor 3 via a steam-heated line 2. The cycle gas mixture leaving the reactor, which comprised essentially ethylene, vinyl acetate monomer, acetic acid, carbon dioxide, oxygen and inerts, was fed via line 4 to the preliminary dewatering column 5. The mixture was separated in the preliminary dewatering column 5, and the bottom product comprising essentially VAM, acetic acid and water was fed via line 8 to the crude vinyl acetate vessel 17, and, after transfer via line 18 into the azeotrope column 19, was separated into a VAM fraction and an acetic acid fraction, which were each worked up further in process steps which are not shown here.

The top product of the preliminary dewatering column 5 was withdrawn and freed of gaseous VAM by means of scrubbing with acetic acid in the downstream cycle gas scrubber 6. The gas mixture (cycle gas) consisted, after the cycle gas scrubbing, essentially of ethylene with a $CO_2$ content amounting to about 12% by volume, and was compressed about 3 bar higher with the cycle gas compressor 7. The majority of the cycle gas was recycled via line 14 into the acetic acid saturator 1. A proportion of about 12% by volume of the cycle gas was branched off from the pressure side of the cycle gas compressor 7 and transferred via line 8 into the water scrubber 9, and treated there with acetic acid and then water to remove residual vinyl acetate monomer. The bottom product comprising acetic acid, water and vinyl acetate monomer was introduced via line 15 directly into the preliminary dewatering column 5. (The broken line 16 shows the embodiment customary in the art, in which the bottom product of the water scrubber 9 is transferred into the crude vinyl acetate monomer vessel 17 and then separated in the azeotrope column 19.)

The top product of the water scrubber 9 was transferred via line 10 into the $CO_2$ scrubber 11, which, in a conventional manner, possessed a potassium carbonate-filled absorption unit and a desorber. After the $CO_2$ scrubbing, the cycle gas substream had a $CO_2$ content of 2% by volume and a pressure of 9 to 11 bar abs. Upstream of the recycling via line 12 into the cycle gas line 14, an ejector 13 was used to inject the entire ethylene feed with a pressure of 20 to 25 bar abs.

The energy saving in the cycle gas compressor 7 was approx. 1000 MWh per year.

The invention claimed is:

1. A process for preparing vinyl acetate monomer in a heterogeneously catalyzed, continuous gas phase process by reacting ethylene with acetic acid and oxygen in a reactor, and
   a) separating the product gas stream comprising essentially ethylene, vinyl acetate monomer, acetic acid, water, carbon dioxide and further inert gases in different distillation processes comprising a preliminary dewatering column, a cycle gas scrubber and an azeotrope column, and
   b) recycling an ethylene- and $CO_2$-containing cycle gas stream into the reactor, by
   c) compressing the cycle gas stream in a cycle gas compressor before recycling into the reactor, and
   d) branching off a substream of the cycle gas on the suction side or the pressure side of the cycle gas compressor and feeding it to a $CO_2$ scrubbing, and
   e) prior to the $CO_2$ scrubbing, washing it in a water scrubber,
   wherein
   f) the substream, after the $CO_2$ scrubbing, is supplied to the cycle gas via a jet compressor, together with ethylene as the motive medium, on the pressure side of the cycle gas compressor and downstream of the withdrawal of the substream to the $CO_2$ scrubbing.

2. The process according to claim 1, wherein
   g) the bottom product from the water scrubber is fed directly to the preliminary dewatering column.

3. The process according to claim 1, wherein the entire ethylene feed which is supplied to the cycle gas stream upstream of the reactor is supplied via the jet compressor.

4. The process according to claim 1, wherein the bottom product from the water scrubber is heated by means of heat exchange with the cycle gas and is fed to the preliminary dewatering column.

5. The process according to claim 2, wherein the entire ethylene feed which is supplied to the cycle gas stream upstream of the reactor is supplied via the jet compressor.

6. The process according to claim 2, wherein the bottom product from the water scrubber is heated by means of heat exchange with the cycle gas and is fed to the preliminary dewatering column.

7. The process according to claim 3, wherein the bottom product from the water scrubber is heated by means of heat exchange with the cycle gas and is fed to the preliminary dewatering column.

8. The process according to claim 5, wherein the bottom product from the water scrubber is heated by means of heat exchange with the cycle gas and is fed to the preliminary dewatering column.

\* \* \* \* \*